(12) United States Patent
Dickson et al.

(10) Patent No.: US 7,265,145 B2
(45) Date of Patent: Sep. 4, 2007

(54) SUBSTITUTED PIPERIDINES AND PYRROLIDINES AS CALCIUM SENSING RECEPTOR MODULATORS AND METHOD

(75) Inventors: John K. Dickson, Apex, NC (US); R. Michael Lawrence, Yardley, PA (US); Jacques Y. Roberge, Princeton, NJ (US); David P. Rotella, Newtown, PA (US); Wu Yang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 546 days.

(21) Appl. No.: 10/854,689

(22) Filed: May 26, 2004

(65) Prior Publication Data

US 2004/0259860 A1 Dec. 23, 2004

Related U.S. Application Data

(60) Provisional application No. 60/473,905, filed on May 28, 2003.

(51) Int. Cl.
*A61K 41/40* (2006.01)
*C07D 207/18* (2006.01)
(52) U.S. Cl. ...................... 514/408; 548/565
(58) Field of Classification Search ................ 514/408; 548/565
See application file for complete search history.

(56) References Cited

U.S. PATENT DOCUMENTS

| 4,411,890 A | 10/1983 | Momany | 514/17 |
| 4,616,017 A * | 10/1986 | Baldwin et al. | 514/253.01 |
| 5,688,938 A | 11/1997 | Brown et al. | 536/23.5 |
| 5,763,569 A | 6/1998 | Brown et al. | 530/324 |
| 6,022,894 A | 2/2000 | Del Mar et al. | 514/524 |
| 6,031,003 A | 2/2000 | Nemeth et al. | 514/579 |
| 6,211,244 B1 | 4/2001 | Van Wagenen et al. | 514/649 |
| 7,053,212 B2 * | 5/2006 | Cameron et al. | 544/58.1 |
| 7,105,537 B2 * | 9/2006 | Gavai et al. | 514/314 |

FOREIGN PATENT DOCUMENTS

| EP | 0342613 B1 | 11/1992 |
| EP | 0449011 B1 | 10/1997 |
| WO | WO89/07110 | 8/1989 |
| WO | WO89/07111 | 8/1989 |
| WO | WO93/04081 | 3/1993 |
| WO | WO94/18959 | 9/1994 |
| WO | WO97/37967 | 10/1997 |
| WO | WO98/45255 | 10/1998 |
| WO | WO99/51241 | 10/1999 |
| WO | WO99/51569 | 10/1999 |
| WO | WO 00/45816 | 8/2000 |
| WO | WO 01/08673 A1 | 2/2001 |
| WO | WO 2005/115975 | * 12/2005 |

OTHER PUBLICATIONS

Bodkin et al. "Preparation of substituted 1-phenoxy . . . " Ca 135:210941 (2001).*
Yang et al. "Discovery and structure activity . . . " Bioorg. Med. chem. Lett. v.15, pp. 1225-1228 (2005).*
Arndt, D., "Mangan-Verbindungen als Oxidationsmittel in der organischen Chemie", Methoden der Organischen Chemie (Houben-Weyl), Fourth Edition, vol. 4, Part 1b, Georg Thieme Verlag, Stuttgart, publ., Müller, E., ed., pp. 466-672 (1975).
Betts, M.J. et al., "'Hidden' axial chirality as a stereodirecting element in reactions involving enol(ate) intermediates. Part 2. Cyclisation reactions of methyl (4R)-3-(2-diazo-3-oxobutanoyl)-1,1-dioxo-1$\lambda^6$, 3- (and 1-oxo-1$\lambda^4$, 3-) thiazolidine-4-carboxylates", J. Chem. Soc., Perkin Trans. 1, pp.

(Continued)

*Primary Examiner*—Celia Chang
(74) *Attorney, Agent, or Firm*—Maureen P. O'Brien

(57) ABSTRACT

Compounds are provided which are antagonists of the calcium sensing receptor, and have the general formula wherein
m is 0, 1, 2, 3 or 4;
each X is independently selected from the group consisting of hydrogen, halo, cyano, nitro, $OCF_3$, hydroxy, amino, carboxyl, alkyl, alkenyl, alkynyl, cycloalkyl, cycloheteroalkyl, haloalkyl, alkoxy, alkoxycarbonylalkyl, hydroxycarbonylalkyl, aryl, arylalkyl, heteroaryl, heteroarylalkyl, cycloalkylalkyl, $R^1O$, $R^1R^2N$, $R^1OCO$, $R^1CO$, $R^1R^2NCO$, $R^1R^2NCONR^{2a}$, $R^1OCONR^{2a}$, $R^1CONR^{2a}$, $R^1S$, $R^1SO$, $R^1SO_2$, $R^1R^2NSO_2$, $R^1R^2NSO_2NR^{2a}$, and $R^1SO_2NR^{2a}$;
$R^1$ is alkyl, alkenyl, alkynyl, cycloalkyl, cycloheteroalkyl, aryl, heteroaryl, arylalkyl, or heteroarylalkyl;
$R^2$ and $R^{2a}$ are the same or different and are independently selected from hydrogen, alkyl, alkenyl, alkynyl, cycloalkyl, cycloheteroalkyl, aryl, heteroaryl, arylalkyl, or heteroarylalkyl;
n is 1, 2, or 3;
W is O or H,$R^3$;
$R^3$ is hydrogen or hydroxyl;
Ar is a substituted or unsubstituted aryl group or a substituted or unsubstituted heteroaryl group;
Q is hydrogen, F, or hydroxyl.

In addition, a method for using these compounds to treat diseases associated with abnormal or mineral homeostasis is also provided.

8 Claims, No Drawings

OTHER PUBLICATIONS

Brown, E.M. et al., "Cloning and characterization of an extracellular $Ca^{2+}$-sensing receptor from bovine parathyroid", Nature, vol. 366, pp. 575-580 (1993).

Bundgaard, H. Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Cagniant, P. et al., "No. 50. Sur la synthése de quelques amines arylaiphatiques dérivées du β- méthyl-naphtaléne", Bull. Soc. Chim. Fr., pp. 349-353 (1943).

Edwards, J.P. et al., "Nonsteroidal Androgen Receptor Agonists Based on 4-(trifluoromethyl)-2H- pyrano[3,2-g]quinolin-2-one", Bioorganic & Medicinal Chemistry Letters, vol. 9, pp. 1003-1008 (1999).

Florvall, L. et al., "Selective Monoamine Oxidase Inhibitors. 3. Cyclic Compounds Related to 4-Aminophenethylamine. Preparation and Neuron-Selective Action of Some 5-(2-Aminoethyl)-2,3-dihydroindoles", J. Med. Chem., vol. 29, No. 8, pp. 1406-1412 (1986).

Gowen, M. et al., "Antagonizing the parathyroid calcium receptor stimulates parathyroid hormone secretion and bone formation in osteopenic rats", The Journal of Clinical Investigation, vol. 105, No. 11, pp. 1595-1604 (2000).

Greene, T.W. et al., Protecting Groups in Organic Synthesis, Third Edition, John Wiley & Sons, Inc., publ. (1999) (table of contents).

Greenstein, J.P. et al., Chemistry of the Amino Acids, vol. 3, Robert E. Krieger Publishing Company, Inc., publ., pp. v-xiii (table of contents) (1984).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, pp. 210-212 (1999).

Hudlický, M., Oxidations in Organic Chemistry: ACS Monograph 186, American Chemical Society, publ., pp. ix-xiii (table of contents) (1990).

Larock, R.C., Comprehensive Organic Transformations: A Guide to Functional Group Preparations, VCH Publishers, Inc., publ., pp. xiii-xxviii (table of contents) (1989).

Lee, D.G., Chapter 11: "Phase Transfer Assisted Permanganate Oxidations", Oxidation in Organic Chemistry, Part D, Academic Press, publ., Trahanovsky, W.S., ed., pp. 147-204 (1982).

Moed, H.D. et al., "Synthesis of β-phenyl-ethylamine Derivaties. III) Bronchodilators", Recl. Trav. Chim. Pays-Bas, vol. 74, pp. 919-936 (1955).

Neer, R.M. et al., "Effect of Parathyroid Hormone (1-34) on Fractures and Bone Mineral Density in Postmenopausal Women with Osteoporosis", The New England Journal of Medicine, vol. 344, No. 19, pp. 1434-1441 (2001).

Nichols, D.E. et al., "Effects of Certain Hallucinogenic Amphetamine Analogues on the Release of [$^3$H]Serotonin from Rat Brain Synaptosomes", J. Med. Chem., vol. 25, No. 5, pp. 530-535 (1982).

Norris, R.K. et al., "Kinetics and Stereochemistry of Elimination of Nitrous Acid from 1-p- Nitrophenyl-2-nitroethyl Derivatives", Aust. J. Chem., vol. 39, pp. 281-294 (1986).

Stewart, R., Chapter 1: "Oxidation by Permanganate", Oxidation in Organic Chemistry, Part A, Academic Press, publ., Wiberg, K.B., ed., pp. 1-68 (1965).

Wermuth, C.G. et al., Chapter 31: "Designing Prodrugs and Biprecursors I: Carrier Prodrugs", The Practice of Medicinal Chemistry, Academic Press, publ., Wermuth, C.G., ed., pp. 671-696 (1996).

Whitfield, J.F. et al., "Parathyroid Hormone, Its Fragments and Their Analogs for the Treatment of Osteoporosis", Treat. Endocrinol., vol. 1, No. 3, pp. 175-190 (2002).

Zaragoza, F. et al., "(Cyanomethyl)trialkylphosphonium Iodides: Efficient Reagents for the Intermolecular Alykylation of Amines with Alcohols in Solution and on Solid Phase", J. Org. Chem., vol. 66, No. 7, pp. 2518-2521 (2001).

* cited by examiner

SUBSTITUTED PIPERIDINES AND PYRROLIDINES AS CALCIUM SENSING RECEPTOR MODULATORS AND METHOD

CROSS-REFERENCE TO RELATED APPLICATION

This application claims the benefit of U.S. Provisional Application No. 60/473,905 filed May 28, 2003, incorporated herein by reference in its entirety.

FIELD OF THE INVENTION

The present invention relates to novel substituted piperidine and pyrrolidine compounds, which are modulators of the calcium sensing receptor, pharmaceutical compositions containing these compounds, and a method for using these compounds to treat diseases or disorders associated with abnormal bone or mineral homeostasis.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "$[Ca^{2+}]$") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in $[Ca^{2+}]$ then acts as a negative feedback signal, depressing PTH secretion. The reciprocal relationship between $[Ca^{2+}]$ and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in $[Ca^{2+}]$ has been confirmed (see Brown et al., Nature 366:574, 1993). In parathyroid cells, this protein, the calcium sensing receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, as reviewed in Nemeth et al., Cell Calcium 11:319, 190. Specifically, the osteoclast in bone, the juxtaglomerular, proximal tubule cells in the kidney, the keratinocyte in the epidermis, the parafollicular cell in the thyroid, intestinal cells, and the trophoblast in the placenta, have the capacity to sense changes in $[Ca^{2+}]$. It has been suggested that cell surface calcium sensing receptors may also be present on these cells, imparting to them the ability to detect and to initiate or enable a response to changes in $[Ca^{2+}]$.

Accordingly, compounds which mimic the effects of extracellular $Ca^{2+}$ on a calcium sensing receptor molecule may be useful as calcium modulators which are active at $Ca^{2+}$ receptors. Such compounds could be useful in the treatment of various disease states characterized by abnormal levels of one or more components, e.g., polypetides, such as hormones, enzymes or growth factors, the expression and/or secretion of which is regulated or affected by activity at one or more $Ca^{2+}$ receptors. Target diseases or disorders for these compounds include diseases involving abnormal bone and mineral homeostasis.

Abnormal calcium homeostasis may be characterized by one or more of the following activities: abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels, such as PTH and calcitonin; and an abnormal change in the response elicited by messengers which affect serum calcium levels.

In extensive animal experiments and in clinical trials, intermittent injection of low doses of PTH has been shown to be a safe and effective stimulator of bone formation (see Whitfiled J F, et al. (2002) Treat Endocrinol (2002) 1(3): 175-190). A double blind, randomized, placebo-controlled trial in postmenopausal women, the PTH peptide fragment (1-34) was shown to reduce the risk of spine fractures and non-traumatic, non-spine fractures 65% and 54%, respectively (Neer R M, et al. (2001) N Engl J Med 344:1434-1441.). In contrast to the anabolic effects observed after intermittent administration, it is well documented that continuous exposure to the hormone results in increases in bone turnover with a subsequent loss in bone mass.

Other than applying a PTH peptide fragment, conceivably, one could make use of the endogenous stores of PTH in the parathyroid gland, in order to stimulate bone formation through the release of PTH.

Proof-of-principle for the calcilytic approach includes a study in osteopenic ovariectomized (OVX) rats in which oral administration of a calcilytic agent NPS-2143 (Gowen M, et al. (2000) J. Clin. Invest. 105:1595-1604) resulted in an increase in bone mass in the presence of an anti-resorptive agent. Intravenous bolus injection of NPS-2143 resulted in a transient increase in serum PTH compatible with the anabolic profile of the hormone. These results indicate that calcilytic agents can serve as a novel class of anabolic agents for the treatment of established osteoporosis.

Thus, the identification of compounds which demonstrate activity as calcium sensing receptor modulators, preferably calcium sensing receptor antagonists, would be of significant value for the treatment of diseases or disorders associated with abnormal bone or mineral homeostasis.

SUMMARY OF THE INVENTION

In accordance with the present invention, compounds are provided which are capable of modulating the function of a calcium sensing receptor, which compounds are preferably antagonists of the calcium sensing receptor, and have the general formula I

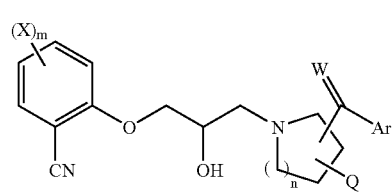

wherein m is 0, 1, 2, 3 or 4;

each X is independently selected from the group consisting of hydrogen, halo, cyano, nitro, $OCF_3$, hydroxy, amino, carboxyl, alkyl, alkenyl, alkynyl, cycloalkyl, cycloheteroalkyl, haloalkyl, alkoxy, alkoxycarbonylalkyl, hydroxycarbonylalkyl, aryl, arylalkyl, heteroaryl, heteroarylalkyl, cycloalkylalkyl, $R^1O$, $R^1R^2N$, $R^1OCO$, $R^1CO$, $R^1R^2NCO$, $R^1R^2NCONR^{2a}$, $R^1OCONR^{2a}$, $R^1CONR^{2a}$, $R^1S$, $R^1SO$, $R^1SO_2$, $R^1R^2NSO_2$, $R^1R^2NSO_2NR^{2a}$, and $R^1SO_2NR^{2a}$;

$R^1$ is alkyl, alkenyl, alkynyl, cycloalkyl, cycloheteroalkyl, aryl, heteroaryl, arylalkyl, or heteroarylalkyl;

$R^2$ and $R^{2a}$ are the same or different and are independently selected from hydrogen, alkyl, alkenyl, alkynyl, cycloalkyl, cycloheteroalkyl, aryl, heteroaryl, arylalkyl, or heteroarylalkyl;

n is 1, 2, or 3;

W is O or $H,R^3$;

$R^3$ is hydrogen or hydroxyl;

Ar is a substituted or unsubstituted aryl group or a substituted or unsubstituted heteroaryl group;

Q is hydrogen, F, or hydroxyl;

with the proviso that when n is 2 or 3, W is $H,R^3$, $R^3$ is hydrogen, and Q is hydrogen.

The definition of formula I above being inclusive of all pharmaceutically acceptable salts, stereoisomers and pro-drug esters of formula I.

The compounds of formula I function as modulators of the calcium sensing receptor. Preferably, the compounds of formula I exhibit activity as antagonists of the calcium sensing receptor and may be used in the treatment of diseases or disorders associated with calcium sensing receptor activity, such as abnormal bone and mineral homeostasis, particularly, hypoparathyroidism, osteosarcoma, chondrosarcoma, periodontal disease, fracture healing, osteoarthritis, Paget's disease, osteopenia, glucocorticoid-induced osteoporosis, osteomalacia, osteoporosis, metastatic bone disease or joint replacement.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with abnormal bone and mineral homeostasis, such as hypoparathyroidism, osteosarcoma, chondrosarcoma, periodontal disease, fracture healing, osteoarthritis, Paget's disease, osteopenia, glucocorticoid induced osteoporosis, osteomalacia, osteoporosis, metastatic bone disease or joint replacement, wherein a therapeutically effective amount of a compound of formula I is administered to a mammalian species, for example, a human patient or dog or cat in need of treatment.

The compounds of the invention can be used alone, in combination with other compounds of the present invention, or in combination with one or more other agent(s) active in the therapeutic areas mentioned herein.

In addition, a method is provided for preventing, inhibiting or treating the diseases as defined above and hereinafter, wherein a therapeutically effective amount of a combination of a compound of formula I and another type of therapeutic agent, is administered, concurrently or sequentially, to a mammalian species, for example, a human patient or dog or cat in need of treatment.

Preferred are compounds of formula I wherein:

X is independently selected from the group consisting of hydrogen, halo, alkyl, alkenyl, alkynyl, cycloalkyl, cycloheteroalkyl, haloalkyl, alkoxy, alkoxycarbonylalkyl, hydroxycarbonylalkyl, aryl, heteroaryl, $R^1R^2NCO$, $R^1CONR^2$, $R^1R^2NSO_2$, and $R^1SO_2NR^{2a}$;

$R^1$ is alkyl, cycloalkyl, cycloheteroalkyl, aryl, heteroaryl, arylalkyl, or heteroarylalkyl;

$R^2$ and $R^{2a}$ are the same or different and are independently selected from hydrogen, alkyl, cycloalkyl, cycloheteroalkyl, aryl, heteroaryl, arylalkyl, or heteroarylalkyl;

m is 0, 1, or 2;

n is 1 or 2;

W is $H,R^3$;

$R^3$ is hydrogen or hydroxyl;

Ar is a substituted or unsubstituted phenyl group; and

Q is hydrogen, F, or hydroxyl.

Examples of preferred compounds include the following

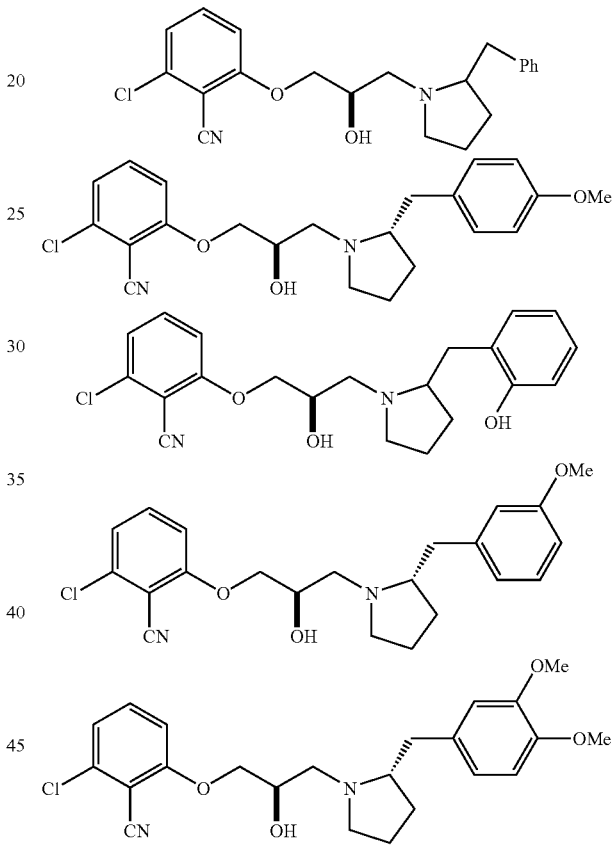

DETAILED DESCRIPTION OF THE INVENTION

The following definitions apply to the terms as used throughout this specification, unless otherwise limited in specific instances.

The term "alkyl" or "lower alkyl" as employed herein, alone or as part of another group, includes both straight and branched chain hydrocarbons, containing 1 to 12 carbons, preferably 1 to 8 carbons, more preferably 1 to 4 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Alkyl may be optionally substituted with one, two, three or four substituents (which may be the same or different) commonly attached to such chains, such as, but not limited to halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio, carboxyl, and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

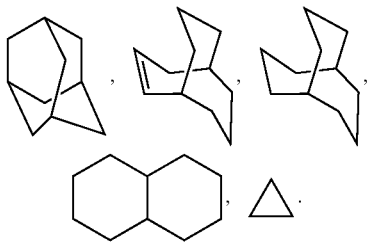

Cycloalkyl may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included for alkyl.

The term "halogen" or "halo" as used herein alone or as part of another group refers to chlorine, bromine, fluorine, and iodine.

Unless otherwise indicated, the term "aryl", "aromatic" or "Ar" as employed herein alone or as part of another group refers to monocyclic and polycyclic (conjugated or fused) aromatic groups containing 5 to 14 carbons in the ring portion (such as phenyl or naphthyl, including 1-naphthyl and 2-naphthyl) and may optionally include one to three additional rings fused to a carbocyclic ring or a heterocyclic ring (such as aryl, cycloalkyl, heteroaryl or cycloheteroalkyl rings, for example

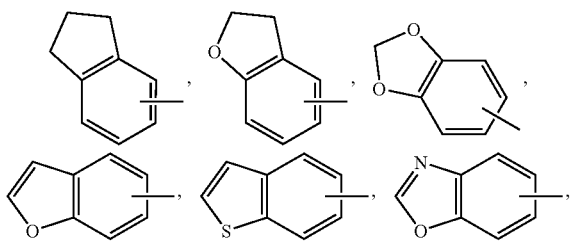

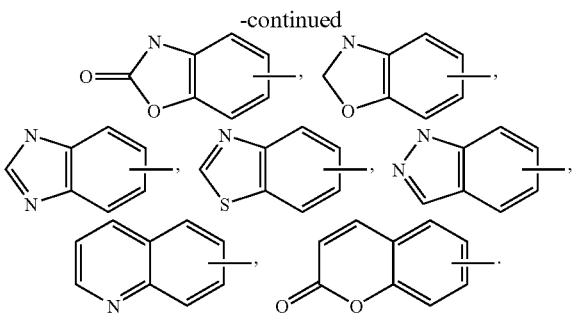

Aryl may be optionally substituted through available carbon atoms with one or more substituents, such as hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, heteroarylalkyl, aryloxy, aryloxyalkyl, alkoxyalkyl, arylalkoxy, alkoxycarbonyl, aryloxycarbonyl, arylalkoxycarbonyl, arylalkenyl, heteroarylalkenyl, heteroarylheteroaryl, heteroaryloxy, heteroarylalkoxy, heteroaryloxyalkyl, aminocarbonylalkyl, aminocarbonylaryl, arylthio, arylalkylthio, heteroarylalkylthio, arylazo, hydroxy, nitro, cyano, carboxyl, carboxylalkoxy, alkoxycarbonylalkoxy, amino, substituted amino, wherein the amino includes 1 or 2 substituents such as alkyl, aryl (or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, alkylsulfonyl, arylsulfonyl, heteroarylsulfonyl, cycloheteroalkylsulfonyl, alkylsulfinyl, arylsulfinyl, arylsulfinylalkyl, arylsulfonylamino, arylsulfonaminocarbonyl and/or any of the alkyl substituents set out herein.

The term "fused" refers to aromatic or heteroaromatic rings that share a pair of carbon atoms, and includes multiple fused aromatic or heteroaromatic rings, for example naphthalene or naphthyridine.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. Heteroaryl may be optionally substituted with one or more substituents such as any of the alkyl or aryl substituents set out above. Examples of heteroaryl groups include the following:

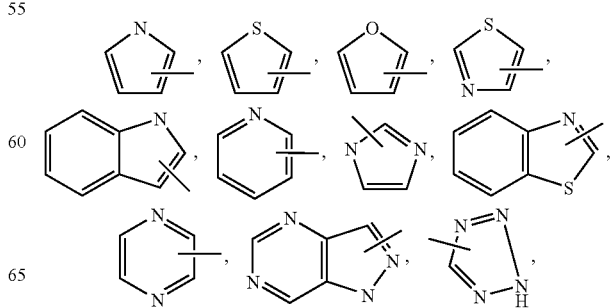

-continued

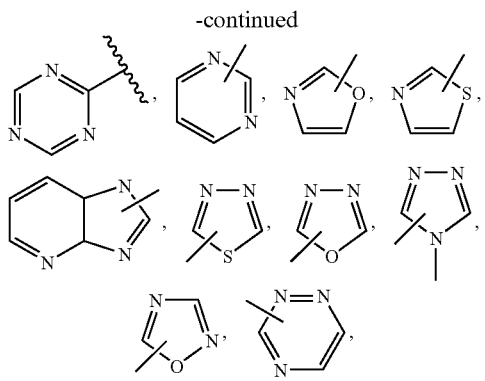

and the like.

Unless otherwise indicated, the term "alkoxy", "aryloxy" or "arylalkoxy" as employed herein alone or as part of another group includes any of the above alkyl, arylalkyl or aryl groups linked to an oxygen atom.

Unless otherwise indicated, the term "alkylthio" or "arylthio" as employed herein alone or as part of another group includes any of the above alkyl, arylalkyl or aryl groups linked through a sulfur atom.

Unless otherwise indicated, the term "alkylamino" or "arylamino" as employed herein alone or as part of another group includes any of the above alkyl, aryl or arylalkyl groups linked through a nitrogen atom.

Unless otherwise indicated, the term "haloalkyl" or "haloalkoxy" as employed herein alone or as part of another group includes a halo group, linked through an alkyl group or alkoxy group, respectively.

The term "cyano," as used herein, refers to a —CN group.

The term "carboxyl" denotes —C(O)O—.

The term "nitro" as used herein, refers to a —NO$_2$ group.

The term "hydroxy" as used herein, refers to —OH.

The term "amino" refers to a group of the formula —NZ$_1$Z$_2$ wherein Z$_1$ and Z$_2$ are each hydrogen, or Z$_1$ and Z$_2$ may each independently be alkyl, aryl or any of the substituents described for alkyl or aryl above.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker (CH$_2$)$_p$ (where p is 1, 2 or 3), such as

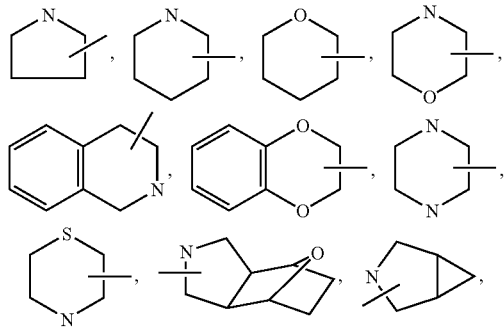

-continued

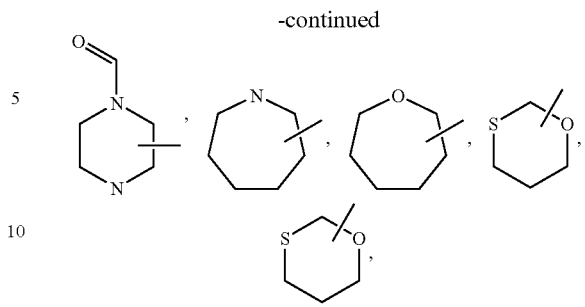

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

The term "cycloheteroalkylalkyl" as used herein alone or as part of another group refers to cycloheteroalkyl groups as defined above linked through a C atom or heteroatom to a (CH$_2$)$_p$ chain where p is 1 to 6.

The term "heteroarylalkyl" or "heteroarylalkenyl" as used herein alone or as part of another group refers to a heteroaryl group as defined above linked through a C atom or heteroatom to a —(CH$_2$)$_p$— chain, alkylene or alkenylene as defined above.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The L linking group includes alkylene groups, as defined herein, each of which may optionally include an oxygen or nitrogen or sulfur in the normal chain, which may optionally include 1, 2, or 3 substituents which include alkyl, alkenyl, halogen, cyano, hydroxy, alkoxy, amino, thioalkyl, keto, C$_3$-C$_6$ cycloalkyl, alkylcarbonylamino or alkylcarbonyloxy; the alkyl substituent may be an alkylene moiety of 1 to 6 carbons which may be attached to one or two carbons in the alkylene group to form a cycloalkyl group therewith.

Examples of L alkylene, groups include

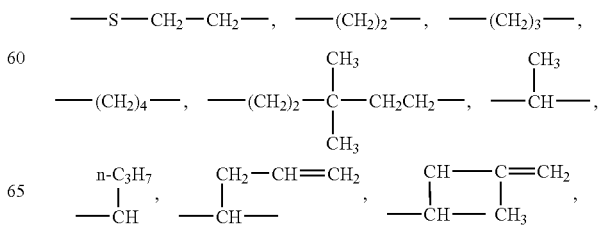

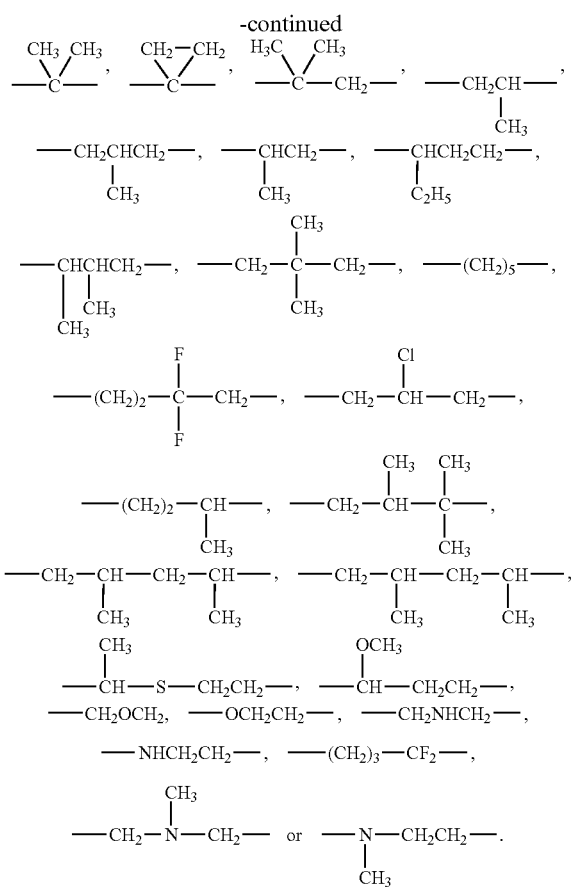

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di-, or tri-lower alkylamine, for example ethyl, tertbutyl, diethyl, diisopropyl, triethyl, tributyl or dimethylpropylamine, or a mono-, di-, or trihydroxy lower alkylamine, for example mono-, di-, or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogen sulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985); and

*A Textbook of Drug Design and Development*, P. Krogsgaard-Larson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatography or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

Compounds of the formula I may be prepared via coupling of an appropriately substituted epoxide II with an appropriately substituted amine derivative III in the presence of an appropriate inert organic solvent as shown in Scheme 1. The reaction is carried out employing a molar ratio of II:III within the range from about 50:1 to about 1:1, preferably from about 5:1 to about 1:1, at a temperature within the range from about 20 to about 200° C., preferably from about 60 to about 120° C.

or OMs. The reaction is carried out employing a molar ratio of V:IV within the range from about 10:1 to about 1:1, preferably from about 5:1 to about 1:1, at a temperature within the range from about 0 to about 120° C., preferably from about 20 to about 100° C., in the presence of an inert organic solvent such as acetone, acetonitrile or dioxane, preferably acetone. Cyanophenols of the formula IV can be prepared by oxime formation followed by dehydration on the aldehyde VI, which is available via formylation of the appropriately substituted phenol VII. Alternatively, treatment of the aryl fluoride VIII with sodium or potassium acetate followed by hydrolysis may provide cyanophenols of the formula IV. The reaction is carried out employing a molar ratio of VIII:acetate within the range from about 1:1 to about 10:1, preferably from about 5:1 to about 1:1, at a temperature within the range from about 20 to about 150° C., preferably from about 50 to about 100° C., in the presence of an inert organic solvent such as acetonitrile.

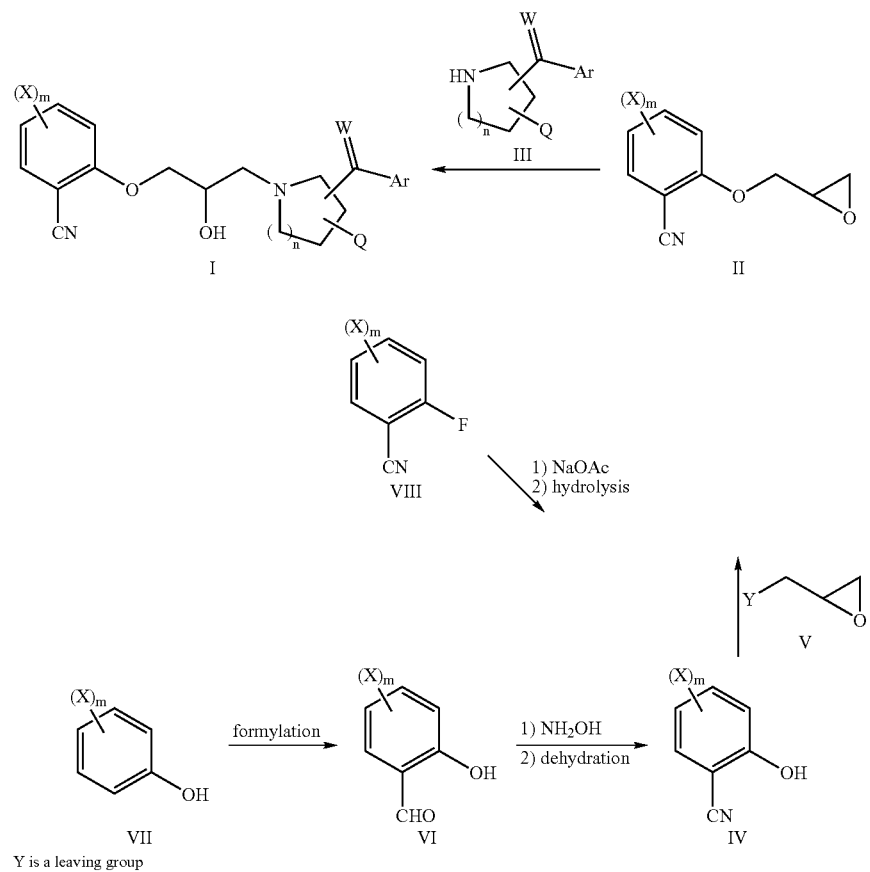

SCHEME 1

Y is a leaving group

Examples of suitable solvents include methanol, ethanol, isopropanol or butanol, preferably isopropanol.

Amines of the formula III are either commercially available, known in the literature, or can be prepared according to the synthesis of similar analogs prepared in the literature or described herein.

Synthesis of epoxides of the formula II can be accomplished by reaction of the phenol IV with the functionalized epoxide V, where Y is a leaving group such as Cl, Br, OTs,

UTILITIES & COMBINATIONS

A. Utilities

Diseases or disorders which can be treated by modulating calcium sensing receptor activity can be identified based on the functional responses of cells regulated by calcium receptor activity. Functional responses of cells regulated by the calcium sensing receptor are known in the art, including parathyroid hormone ("PTH") secretion by parathyroid cells, calcitonin secretion by C-cells, bone reabsorption by osteoclasts and $Ca^{2+}$ secretion by kidney cells.

The compounds of the present invention preferably function as modulators of the calcium sensing receptor, particularly as antagonists of the calcium sensing receptor. Accordingly, the compounds of the invention may be used to stimulate a functional response by parathyroid cells whereby such cells release PTH, preferably a transient release of PTH. Thus, the compounds of the present invention may be used in the treatment of diseases or disorders which can be affected by modulating one or more activities or functions of a calcium sensing receptor, wherein treatment comprises prevention, partial alleviation or cure of the condition or disorder. Modulation may occur locally, for example with certain tissues of the subject, or more extensively throughout a subject being treated for such a condition or disorder.

The compounds of the present invention can be administered animals, including humans, for the treatment of a variety of conditions and disorders, including, but not limited to bone and mineral-related diseases or disorders, (e.g., hypoparathyroidism, osteosarcoma, chondrosarcoma, periodontal disease, fracture healing, osteoarthritis, Paget's disease, osteopenia, glucocorticoid induced osteoporosis, osteomalacia and osteoporosis); metastatic bone disease; joint replacement; diseases involving excess water reabsorption by the kidney, such as syndrome of inappropriate ADA secretion (SIADH), cirrhosis, congestive heart failure and nephrosis; hypertension; diseases involving abnormally low serum parathyroid levels; preventing and/or decreasing renal toxicity from cationic antibiotics (e.g., amionglycoside antibiotics); renal osteodystrophy; gut motility disorders, such as diarrhea and spastic colon, GI ulcer diseases; GI diseases with excessive calcium absorption; sarcoidosis; autoimmune diseases and organ transplant rejection; inflammatory diseases, such as asthma, rheumatoid arthritis, inflammatory bowel disease, transplant rejection, and chronic obstructive pulmonary disease; and diseases caused by excess gastric acid secretion.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination with other modulators of the calcium sensing receptor or other suitable therapeutic agents useful in the treatment of the aforementioned disorders including anti-osteoporosis agents, cholesterol/lipid lowering agents, growth promoting agents and/or progesterone receptor agonists.

Examples of suitable anti-osteoporosis agents for use in combination with the compounds of the present invention include bisphosphonates (e.g., alendronate, risedronate, ibandronate and zolendrate) parathyroid hormone, PTH fragment, calcitonins, RANK ligand antagonists, TRAP inhibitors and AP-1 inhibitors.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)).

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotonin $5-HT_{1D}$ agonists, such as sumatriptan, or agents which inhibit somatostatin or its release, such as physostigmine and pyridostigmine.

Examples of suitable progesterone receptor agonists for use in combination with the compounds of the present invention include levonorgestrel and medroxyprogesterone acetate (MPA).

The compounds of the present invention may further be used in combination with modulators of bone resorption (e.g., estrogen); selective estrogen receptor modulators (e.g., tamoxifen, lasofoxifene, TSE-424 and raloxifene); or selective androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

In addition, compounds of the present invention may be used in combination with therapeutic agents such as anti-resorptive agents; hormone replacement therapies; vitamin D and analogues thereof (e.g., 1,25-dihydroxy vitamin D3); elemental calcium and calcium supplements; cathepsin K inhibitors; MMP inhibitors; vitronectin receptor antagonists; Src $SH_2$ antagonists; Src kinase inhibitors; vacuolar $H^+$-ATPase inhibitors; PTH and its analogues and fragments; osteoprotegrin; Tibolone; p38 inhibitors; prostanoids; PPAR gamma antagonists or isoflavinoids (e.g., genistein, ipriflavone and testosterone).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal, aerosol, or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day, that can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

EXAMPLES

The following examples serve to better illustrate, but not limit, some of the preferred embodiments of the invention.

The following abbreviations are employed in the Examples:

AcOEt=ethyl acetate

AcOH=acetic acid aq.=aqueous

Ar=argon $BBr_3$=boron tribromide $BF_3$ $OEt_2$=boron trifluoride etherate

Bn=benzyl

BOC=tert-butoxycarbonyl

BOP reagent=benzotriazol-1-yloxy-tris (dimethylamino) phosphonium hexafluorophosphate br=broad Bu=butyl c=concentration ° C.=degrees Centigrade CAN=ceric ammonium nitrate CBZ=carbobenzyloxy or carbobenzoxy or benzyloxycarbonyl $CDCl_3$=chloroform-d $CD_3OD$=methanol-$d_4$ $CH_2Cl_2$=dichloromethane $CHCl_3$=chloroform $CH_3CN$=acetonitrile $Cs_2CO_3$=cesium carbonate d=day(s) or doublet DBU=1,8-diazabicyclo[5.4.0]undec-7-ene DEAD=diethylazodicarboxylate DIAD=diisopropylazodicarboxylate DIBAL=diisobutylaluminum hydride DMAP=4-dimethylaminopyridine DME=1,2-dimethoxyethane DMF=dimethylformamide DMSO=dimethylsulfoxide EDC=3-ethyl-3'-(dimethylamino)propylcarbodiimide hydrochloride ES+=electrospray positive ionization Et=ethyl $Et_3N$=triethylamine EtOAc=ethyl acetate $Et_2O$=diethyl ether EtOH=ethanol $Et_3SiH$=triethylsilane FMOC=fluorenylmethoxycarbonyl
g=gram(s)
h=hour(s)
HCl=hydrochloric acid
hex=hexane or hexanes
$HNO_3$=nitric acid
$H_2O$=water
HOAc=acetic acid
HOAT=1-hydroxy-7-azabenzotriazole
HOBT=1-hydroxybenzotriazole hydrate
HPLC=high performance liquid chromatography
$H_3PO_4$=phosphoric acid
$H_2SO_4$=sulfuric acid
Hz=hertz
iPr=isopropyl
$iPr_2NEt$=diisopropylethylamine
iPrOH=isopropanol
$K_2CO_3$=potassium carbonate
KF=potassium fluoride
KHMDS=potassium bis(trimethylsilyl)amide
$KHSO_4$=potassium hydrogen sulfate
KOH=potassium hydroxide
KOTMS=potassium trimethylsilanolate
L=liter(s)
LAH=lithium aluminum hydride
LC/MS=high performance liquid chromatography/mass spectrometry
$LiAlH_4$=lithium aluminum hydride
LiHMDS=lithium bis(trimethylsilyl)amide
LiOH=lithium hydroxide
m=multiplet
M=molar
mCPBA=3-chloroperoxybenzoic acid
Me=methyl
MeOH=methanol
meq=milliequivalent(s)
mg=milligram(s)
$MgCl_2$=magnesium chloride
$MgSO_4$=magnesium sulfate
MHz=megahertz
μL=microliter(s)
min=minute(s)
mL=milliliter(s)
mm=millimeter(s)
mmol=millimole(s)

$MnO_2$=manganese dioxide
mol=mole(s)
mp=melting point
MS or Mass Spec=mass spectrometry
m/z=mass to charge ratio
$N_2$=nitrogen
$NaBH_4$=sodium borohydride
$NaBH(OAc)_3$=sodium triacetoxyborohydride
$NaCNBH_3$=sodium cyanoborohydride
$NaHCO_3$=sodium bicarbonate
NaHMDS=sodium bis(trimethylsilyl)amide
NaOH=sodium hydroxide
NaOEt=sodium ethoxide
NaOMe=sodium methoxide
NaSMe=sodium thiomethoxide
$Na_2SO_4$=sodium sulfate
nBuLi=n-butyllithium
$NEt_3$=triethylamine
$NH_3$=ammonia
$NH_4Cl$=ammonium chloride
$NH_4OH$=ammonium hydroxide
NMM=N-methylmorpholine
NMO=N-methylmorpholine N-oxide
NMP=N-methylpyrrolidinone
NMR=nuclear magnetic resonance
Pd/C=palladium on carbon
$Pd(OAc)_2$=Palladium acetate
Ph=phenyl
$Ph_3P$=triphenylphosphine
$(Ph_3P)_4Pd$=tetrakistriphenylphosphine palladium
$P_2O_5$=phosphorus pentoxide
$POCl_3$=phosphorus oxychloride
Pr=propyl
$PtO_2$=platinum oxide
$PXPd_2$=bis[di-tert-butylphosphinous chloride-κP]-di-μ-chlorodipalladium
$R_f$=retention time
RT=room temperature
s=singlet
sat or sat'd=saturated
$SOCl_2$=thionyl chloride
t=triplet
TBS=tert-butyldimethylsilyl
tBu=tertiary butyl
TFA=trifluoroacetic acid THF=tetrahydrofuran Ti(OiPr)$_4$=titanium isopropoxide TLC=thin layer chromatography TMEDA=N,N,N',N'-tetramethylethylenediamine TMS=trimethylsilyl or trimethylsilane UV=ultraviolet HPLC analysis of the exemplified compounds was carried out under one of the following reverse phase methods, with the appropriate method and retention time noted in the Examples.

Method A: Zorbax SB C18 column (4.6×75 mm), 0-100% B:A (solvent A=90% H$_2$O/MeOH+0.2% H$_3$PO$_4$; solvent B=90% MeOH/H$_2$O+0.2% H$_3$PO$_4$), linear gradient over 8 minutes at 2.5 ml/min, detection at 220 nM.

Method B: YMC S5 ODS column (4.6×50 mm), 0-100% B:A (solvent A=90% H$_2$O/MeOH+0.2% H$_3$PO$_4$; solvent B=90% MeOH/H$_2$O+0.2% H$_3$PO$_4$), linear gradient over 4 minutes at 4.0 ml/min, detection at 220 nM.

Method C: Phenominex Luna C18 column (4.6×50 mm), 0-100% B:A (solvent A=90% H$_2$O/MeOH+0.1% TFA; solvent B=90% MeOH/H$_2$O+0.1% TFA), linear gradient over 4 minutes at 4.0 ml/min, detection at 220 nM.

Example 1

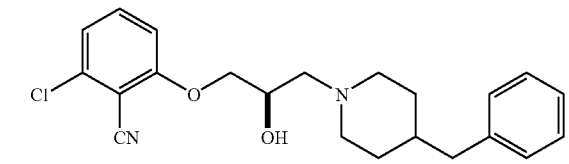

A.

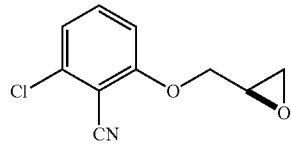

To a mixture of 3-chloro-2-cyanophenol (2.1 g, 13.7 mmol), tetrabutylammonium iodide (0.9 g, 2.4 mmol) and cesium carbonate (11.0 g, 33.8 mmol) in acetonitrile (50 mL) in a round-bottom flask equipped with a condenser was added (R)-epichlorohydrin (4.5 ml, 54 mmol) and the mixture was maintained at reflux for 5 h (oil bath temp 100-105° C.). The mixture was cooled to room temperature, filtered and concentrated under reduced pressure. The residue was diluted in NaOH (0.1 M, 50 mL) and extracted with ether (3×75 mL), dried over sodium sulfate, and filtered over 15 g of silica gel. After concentration, the solid was crystallized from a mixture of hexane/ethyl acetate to give 2.42 g (84%) of the title compound as white needles.

HPLC retention time (Method B)=2.34 min.

LC/MS (ESI) (M+H)$^+$=210.

$^1$H NMR (CDCl$_3$, 500 MHz) δ 7.47 (t, J=8 Hz, 1H), 7.10 (d, J=7 Hz, 1H), 6.94 (d, J=8 Hz, 1H), 4.40 (dd, J=3, 12 Hz, 1H), 4.10(dd, J=5, 11 Hz, 1H),3.38(m, 1H), 2.93 (dd, J=4, 5 Hz, 1H), 2.83 (dd, J=3, 12 Hz, 1H); $^{13}$C NMR (CDCl$_3$, 125 MHz) δ 44.42, 49.66, 69.79, 76.75, 77.00, 77.25, 103.62, 110.70, 113.30, 122.24, 134.22, 138.03, 161.41.

[α]$_D^{25}$=8.8° (c=5.4 mg/ml, methanol).

B.

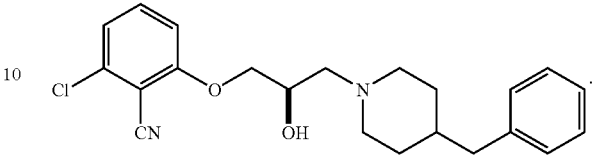

4-Benzylpiperidine (138 mg, 0.8 mmol) was added under nitrogen to a solution of the Part A epoxide (55 mg, 0.26 mmol) in isopropanol (1.6 ml) in a 2 dram vial, and the mixture was shaken at 80° C. overnight. The mixture was diluted with the preparative solvent mixture A (500 μl) and purified by preparative HPLC (YMC S5 ODS column, 20×100 mm, 25 ml/min, 8 min linear gradient from 30% B in A to 100% B [solvent A=90% water, 10% methanol, 0.1% trifluoroacetic acid; solvent B=90% methanol, 10% water, 0.1% trifluoroacetic acid]). The product fractions were combined and the solvent was evaporated. The residue was dissolved in MeOH (3 ml), treated with hydrogen chloride (1 ml, 2M in ethanol) and hydrochloric acid (1 ml, 1N in water), and the mixture was concentrated under reduced pressure. This procedure of dissolution in MeOH and treatment with HCl was repeated to provide 83 mg (75%) of the title compound as a white powder.

HPLC retention time (Method A)=5.25 min.

LC/MS (ESI) (M+H)$^+$=385.

1H NMR (CDCl$_3$, 400 MHz) δ 7.41 (t, J=8.4 Hz, 1H), 7.25-7.05 (m, 6H), 6.84 (d, J=8.8 Hz, 1H), 4.61 (brs, 1H), 4.27 (dd, J=8.8, 3.9 Hz, 1H), 3.90 (t, J=8.8 Hz, 1H), 3.73 (d, J=11.4 Hz, 1H), 3.59 (d, J=11.0 Hz, 1H), 3.31-3.12 (m, 2H), 2.76-2.56 (m, 4H), 2.04-1.60 (m, 5H).

Example 2

A.

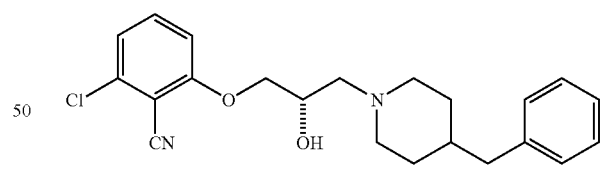

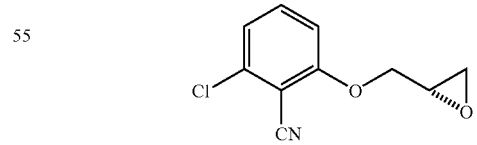

The title compound was prepared from (R)-epichlorohydrin according to the procedure described for the Example 1 Part A compound.

HPLC retention time (Method B)=2.34 min.

LC/MS (ESI) (M+H)$^+$=210.

[α]D$^{25}$=−7.9° (c=6.1 mg/ml, methanol).

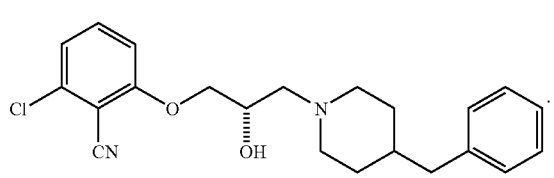

B

The title compound was prepared from the Part A compound according to the procedure described in Example 1.

HPLC retention time (Method A)=5.25 min.

LC/MS (ESI) (M+H)⁺=385.

Example 3

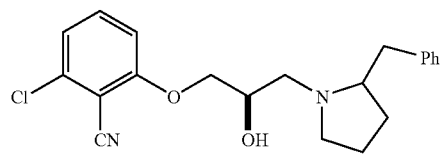

A mixture of Example 1 Part A compound (363 mg, 1.74 mmol) and 2-benzylpyrrolidine (280 mg, 1.73 mmol) in EtOH (5 mL) in a sealed tube was heated to 110° C. for 16 h. The solvent was removed from the cooled reaction mixture, and the resulting residue was purified by flash chromatography (silica gel, 5% MeOH in CH$_2$Cl$_2$) to afford 532 mg (83%) of the title compound as a pale yellow oil as a mixture of diastereomers.

HPLC retention time (Method A)=5.71 min.

LC/MS (ESI) (M+H)⁺=371.

The two diastereomers of the title compound were separated by preparative HPLC using a CHIRALPAK® OD column (5×50 cm) with 20% isopropanol/hexane containing 0.1% triethylamine as an eluent at a flow rate of 50 mL/min to provide diastereomer A and diastereomer B, both as colorless oils.

HPLC retention time of diastereomer A=9.9 min.

HPLC retention time of diastereomer B=19.4 min.

(Method=Chiralcel OD column (4.6×250 mm) with 20% isopropanol/hexane containing 0.1% triethylamine as an eluent at a flow rate of 1 ml/min; detector wavelength=220 nm.)

Diastereomer A was found to have the (R,S)-stereochemistry:

$^1$H NMR (CD$_3$OD, 400 MHz) δ 7.57 (t, J=8.8 Hz, 2H), 7.24-7.11 (m, 7H), 4.11-4.22 (m, 3H), 3.22-3.32 (m, 2H), 3.07 (dd, J=4.0, 13.2 Hz, 1H), 2.66 (m, 1H), 2.32-2.47 (m, 3H), 2.35-2.41 (m, 1H), 1.64-1.78 (m, 3H), 1.45-1.54 (m, 1H). $^{13}$C NMR (CD$_3$OD, 400 MHz) δ 163.63, 141.06, 138.45, 136.15, 130.27, 129.23, 126.98, 122.85, 114.52, 112.37, 103.87, 73.15, 69.75, 68.29, 58.28, 56.26, 41.68, 30.93, 23.27.

Example 4

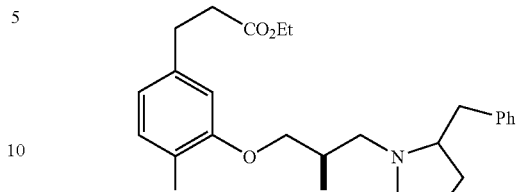

The title compound was prepared according to the procedure described in Example 3 by coupling ethyl (R)-4-cyano-3-(oxiranylmethoxy)benzeneproprionate (PCT Application WO01/53254A1) to 2-benzylpyrrolidine.

HPLC retention time (Method A)=6.14 min.

LC/MS (ESI) (M+H)⁺=437.

$^1$H NMR (CD$_3$OD, 400 MHz) δ 7.45 (d, J=7.9 Hz, 1H), 7.28-7.16 (m, 5H), 6.86 (t, J=7.9 Hz, 2H), 4.15-4.04 (m, 5H), 3.26-3.01 (m, 4H), 2.97 (t, J=6.7 Hz, 2H), 2,81-2.29 (m, 5H), 1.80-1.69 (m, 3H), 1.57-1.51 (m, 1H), 1.23 (t, J=7.1 Hz, 3H).

Example 5

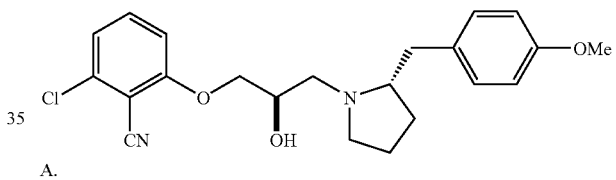

A.

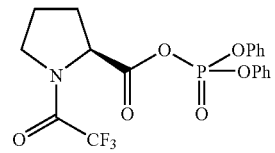

The Part A compound was prepared following the procedure described in the literature (*Bioorg. Med. Chem. Lett.* 1995, 20, 2371-2376).

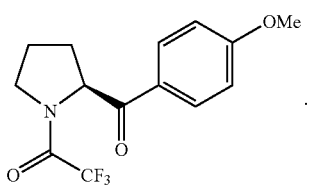

B

To a solution of the Part A compound (1.24 g, 2.87 mmol) in anhydrous THF (10 mL) at −72° C. under Ar was added 4-methoxyphenylmagnesium bromide (0.5 M in THF, 5.75 mL, 2.87 mmol) dropwise, keeping the reaction temperature below −60° C. The reaction was gradually warmed to room temperature, then poured into cold saturated aqueous NH$_4$Cl solution. The organic phase was separated, washed with water and brine, dried over MgSO$_4$, filtered and concentrated. Purification by flash column chromatography (silica gel, 1:2 EtOAc/hexane) provided the title compound as a white solid (490 mg, 60%).

HPLC retention time (Method C)=2.78 min.

LC/MS (ESI) (M+H)⁺=302.

¹H NMR (CDCl₃, 400 MHz) δ 7.88 (d, J=7 Hz, 2H), 6.87 (d, J=7 Hz, 2H), 5.45 (dd, J=4, 9 Hz, 1H), 3.79 (s, 3H), 3.71-3.84 (m, 2H), 2.24-2.27 (m, 1H), 1.96-2.03 (m, 2H), 1.90-1.93 (m, 1H).

C

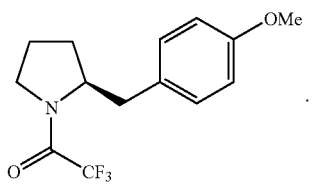

To a solution of the Part B compound (105 mg, 0.35 mmol) in CH₂Cl₂ (2 mL) was added BF₃OEt₂ (0.2 mL), followed by addition of Et₃SiH (3 mL). The reaction was stirred at room temperature for 30 h, then quenched by dropwise addition of saturated aqueous K₂CO₃. The organic layer was separated and dried over MgSO₄, filtered and concentrated. Purification by flash column chromatography (silica gel, 1:2 EtOAc/hexane) provided the title compound as a pale yellow oil (70 mg, 70%).

HPLC retention time (Method C)=3.37 min.

LC/MS (ESI) (M+Na)⁺=310.

¹H NMR (CDCl₃, 400 MHz) δ 7.12 (d, J=6 Hz, 2H), 6.85 (d, J=6 Hz, 2H), 4.33 (m, 1H), 3.64 (m, 1H), 3.56 (m, 1H), 3.04 (dd, J=4, 13 Hz, 1H), 2.67 (dd, J=9, 13 Hz, 1H), 1.87 (m, 3H), 1.43 (m, 1H).

D

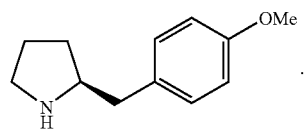

To a solution of the Part C compound (70 mg, 0.24 mmol) in 2-propanol (1 mL) was added concentrated HCl (0.7 mL). The reaction mixture was heated at 80° C. for 16 h, cooled to room temperature, then concentrated in vacuo. The residue was dissolved in methanol (1 mL) and gravity filtered through an CLEAN-UP extraction column (UCT, CUBCX1HL). The column was washed with methanol (10 mL), followed by NH₃ in methanol (3N, 10 mL). The NH₃/MeOH washed fractions were collected and concentrated to yield the title compound as a colorless oil (45 mg, 98%).

¹H NMR (CDCl₃, 400 MHz) δ 7.06 (d, J=8.5 Hz, 2H), 6.75 (d, J=8.5 Hz, 2H), 4.47 (br, 1H), 3.70 (s, 3H), 3.25 (m, 1H), 3.04 (m, 1H), 2.86 (m, 1H), 2.80 (dd, J=7.3, 13.5 Hz, 1H), 2.67 (dd, J=7.3, 13.5 Hz, 1H), 1.77 (m, 3H), 1.40 (m, 1H).

E

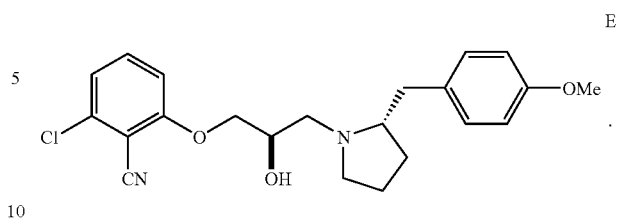

According to the procedure described in Example 3, the Example 1 Part A epoxide was coupled to the Part D compound to provide the title compound (81 mg, 84%).

HPLC retention time (Method A)=5.22 min.

LC/MS (ESI) (M+H)⁺=401.

¹H NMR (CD₃OD, 400 MHz) δ 7.57 (t, J=8.4 Hz, 2H), 7.15 (t, J=8.4 Hz, 2H), 7.09 (dd, J=6.7, 2.0 Hz, 2H), 6.77 (dd, J=6.7, 2.0 Hz, 2H), 4.20-4.12 (m, 3H), 3.73 (s, 3H), 3.31-3.20 (m, 2H), 2.98 (dd, J=13.3, 4.2 Hz, 1H), 2.65 (br, 1H), 2.47-2.35 (m, 3H), 1.72-1.69 (m, 3H), 0.89(m, 1H).

Example 6

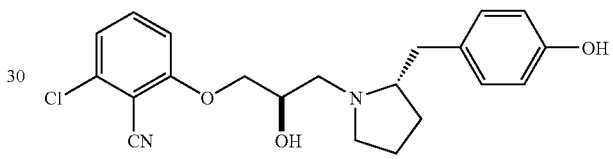

To a solution of the Example 5 compound (68 mg, 0.17 mmol) in dry CH₂Cl₂ (1 mL) at −70° C. under Ar was added BBr₃ (10M in CH₂Cl₂, 1 mL). The reaction mixture was gradually warmed to room temperature, stirred overnight, then concentrated in vacuo. The residue was dissolved in methanol (2 mL) and was purified by preparative HPLC (Shimadzu VP-ODS 20×100 mm column, 30-100% B:A (solvent A=90% H₂O/MeOH+0.1% TFA; solvent B=90% MeOH/H₂O+0.1% TFA); linear gradient over 25 min at 20 mL/min, wavelength=220 nm) to yield the title compound as a white solid (31 mg, 36%).

HPLC retention time (Method A)=4.15 min.

LC/MS (ESI) (M+H)⁺=387.

¹H NMR (CDCl₃, 400 MHz) δ 7.61 (t, J=8.4 Hz, 1H), 7.23 (d, J=8.5 Hz, 1H), 7.17 (d, J=8.6 Hz, 1H), 7.12 (d, J=8.4 Hz, 2H), 6.76 (d, J=8.4 Hz, 2H), 4.42 (m, 1H), 4.24 (dd, J=4.6, 9.9 Hz, 1H), 4.16 (dd, J=5.5, 9.9 Hz, 1H), 3.90 (m, 1H), 3.78 (m, 1H), 3.67 (dd, J=2.4, 13.4 Hz, 1H), 3.29-3.39 (m, 3H), 2.78 (dd, J=11, 13 Hz, 1H), 2.08 (m, 3H), 1.83 (m, 1H).

Example 7

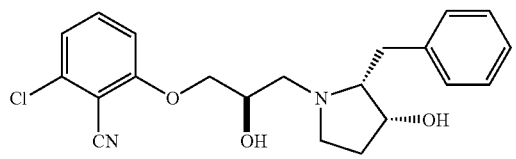

-continued

A.

The Part A compound was prepared according to the procedure in the literature (*J. Chem. Soc. Perkin* 1, 2001, 1421-1430).

B.

The Part B compound was prepared from the Part A compound according to the procedure described for the preparation of the Example 8 Part B compound.

HPLC retention time (Method C)=0.90 min.
LC/MS (ESI) (M+H)$^+$=178.3.

C.

The title compound was prepared according to the procedure described in Example 3.

HPLC retention time (Method A)=4.99 min.
LC/MS (ESI) (M+H)$^+$=387.

$^1$H NMR (CD$_3$OD, 400 MHz) δ 7.61 (t, J=8.4 Hz, 1H), 7.40 (m, 2H), 7.32 (t, J=7.3 Hz, 2H), 7.25-7.22 (m, 2H), 7.16 (d, J=8.5 Hz, 1H), 4.50 (m, 1H), 4.24 (dd, J=4.7, 9.9 Hz, 1H), 4.17 (t, J=2.9 Hz, 1H), 4.12 (dd, J=5.9, 9.9 Hz, 1H), 3.98 (m, 1H), 3.69-3.62 (m, 3H), 3.39-3.21 (m, 3H), 2.30-2.02 (m, 2H).

Example 8

-continued

A.

To a solution of bis-(2-methoxyethyl)aminosulfur trifluoride (BAST) (73 µL, 0.36 mmol) in CH$_2$Cl$_2$ (1 mL) at −76° C. under Ar was added a solution of the Example 7 Part A compound (100 mg, 0.36 mmol) in CH$_2$Cl$_2$ (1 mL). The reaction mixture was stirred at −76° C. for 30 min before being warmed to room temperature and stirred for another 4 h. The reaction was quenched with saturated NaHCO$_3$, then extracted with CH$_2$Cl$_2$. The organic layer was dried over MgSO$_4$, concentrated and purified by preparative HPLC (Shimadzu VP-ODS 20×100 mm column, 20-100% B:A (solvent A=90% H$_2$O/MeOH +0.1% TFA; solvent B=90% MeOH/H$_2$O+0.1% TFA), linear gradient over 25 min at 20 mL/min, wavelength=220 nm) to give the fluoro derivative as a white solid (23 mg, 24%).

HPLC retention time (Method C)=3.67 min.
LC/MS (ESI) (M+H)$^+$=280.

B.

To a solution of the Part A compound (23 mg, 0.08 mmol) in CH$_2$Cl$_2$ (2 mL) at 0° C. was added TFA (2 mL). After 30 min, the reaction mixture was concentrated in vacuo. The residue was dissolved in MeOH and loaded onto a CLEAN-UP extraction column (UTC, CUBCX1HL). The column was washed with MeOH (10 mL), then NH3 in MeOH (2N, 10 mL). The NH$_3$/MeOH washed fractions were condensed to yield the deprotected amine (12 mg, 84%).

HPLC retention time (Method A)=1.47 min.
LC/MS (ESI) (M+H)$^+$=180.

C.

The title compound was prepared according to the procedure described for the preparation of the Example 3 compound (12 mg, 37%).

HPLC retention time (Method A)=4.95 min.
LC/MS (ESI) (M+H)$^+$=389.

$^1$H NMR (CD$_3$OD, 400 MHz) δ 7.62 (t, J=8.0 Hz, 1H), 7.41-7.29 (m, 5H), 7.21 (dd, J=18.3, 8.0 Hz, 2H), 5.19(s, 0.5H), 5.06(s, 0.5H), 4.55-4.49 (m, 1H), 4.31-4.21 (m, 3H), 4.03 (brs, 1H), 3.68-3.58 (m, 3H), 3.41 (d, J=14.0 Hz, 1H), 2.87 (d, J=14.0 Hz, 1H), 2.49-2.43 (m, 2H).

Example 9

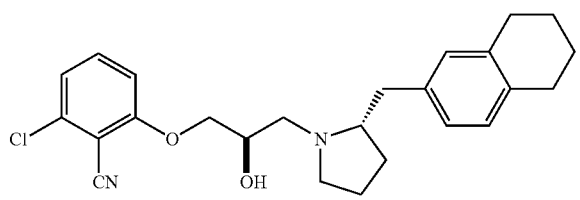

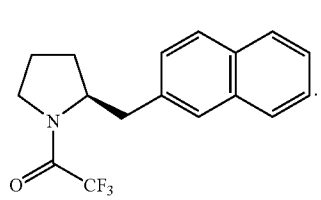

A

The Part A compound was prepared according to the procedure described for the Example 5 Part C compound.

HPLC retention time (Method C)=3.25 min.
LC/MS (ESI) (M+H)+=321.

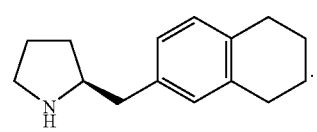

B

A solution of the Part A compound (178 mg, 0.55 mmol) in EtOH (5 mL) was purged with Ar. To this solution was added saturated HCl in ether (1 mL) and 10% palladium on carbon (60 mg, 0.05 mmol). The reaction mixture was stirred under 60 psi of hydrogen for 10 days. The reaction was filtered and the filtrate was loaded onto a CLEAN-UP extraction column (UTC, CUBCX1HL), washed with MeOH, then with 2N NH$_3$ in MeOH. The NH$_3$/MeOH wash solution was condensed to afford a pale yellow oil (30 mg, 25% yield) which was used in the next step without any further purification.

HPLC retention time (Method C)=2.55 min.
LC/MS (ESI) (M+H)+=216.3.

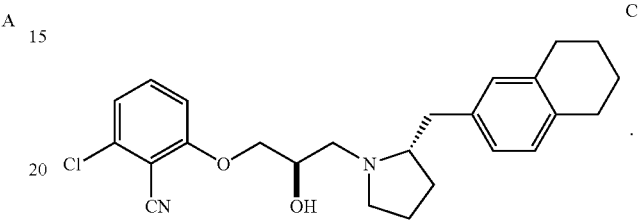

C

The title compound was prepared according to the procedure described in Example 3 (28 mg, 47%).

HPLC retention time (Method A)=6.24 min.
LC/MS (ESI) (M+H)+=425.
$^1$H NMR (CD$_3$OD, 400 MHz) δ 7.61 (t, J=8.4 Hz, 1H), 7.22 (d, J=7.8 Hz, 1H), 7.17 (d, J=8.5 Hz, 1H), 7.03-7.00 (m, 3H), 4.45-4.41 (m, 1H), 4.24-4.13 (m, 2H), 3.92-3.80 (m, 2H), 3.64 (dd, J=13.4, 2.4 Hz, 1H), 3.39-3.30 (m, 3H), 2.86-2.69 (m, 5H), 2.11-2.06 (m, 3H), 1.85-1.74 (m, 5H).

Examples 10 to 23

Examples 10 to 23 set out in Table 1 were prepared according to the general procedures described herein.

TABLE 1

| Example No. | R$^1$ | R$^2$ | HPLC R$_t$ (min) [Method] | LC/MS (ESI) (M + H)+ m/z |
|---|---|---|---|---|
| 10 | 2-CN, 6-Cl-phenyl | 3-benzylpyrrolidin-1-yl | 5.25 [A] | 371 |
| 11 | 2-CN, 6-Cl-phenyl | 4-(3-methoxybenzyl)piperidin-1-yl | 5.90 [A] | 415 |

TABLE 1-continued $$R^1\text{O}\underset{\text{OH}}{\overset{}{\diagdown}}R^2$$

| Example No. | R¹ | R² | HPLC R$_t$ (min) [Method] | LC/MS (ESI) (M + H)⁺ m/z |
|---|---|---|---|---|
| 12 | 2-Cl, 6-CN-phenyl | 4-(2,5-difluorobenzyl)piperidin-1-yl | 5.65 [A] | 421 |
| 13 | 2-Cl, 6-CN-phenyl | 3-benzylpiperidin-1-yl | 5.44 [A] | 385 |
| 14 | 2-Cl, 6-CN-phenyl | 2-(3-fluorobenzyl)pyrrolidin-1-yl | 5.25 [A] | 389 |
| 15 | 2-Cl, 6-CN-phenyl | 2-[(3-fluorophenyl)(hydroxy)methyl]pyrrolidin-1-yl | 4.83 [A] | 405 |
| 16 | 2-Cl, 6-CN-phenyl | 2-(2-methoxybenzyl)pyrrolidin-1-yl | 5.38 [A] | 401 |
| 17 | 2-Cl, 6-CN-phenyl | 2-(2-hydroxybenzyl)pyrrolidin-1-yl | 4.93 [A] | 387 |
| 18 | 2-Cl, 6-CN-phenyl | 2-(3-methoxybenzyl)pyrrolidin-1-yl | 5.22 [A] | 401 |

TABLE 1-continued
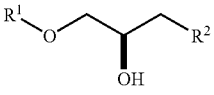
| Example No. | R¹ | R² | HPLC $R_t$ (min) [Method] | LC/MS (ESI) (M + H)⁺ m/z |
|---|---|---|---|---|
| 19 | 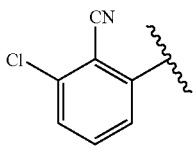 | 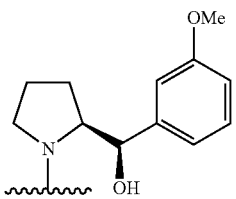 | 4.83 [A] | 417 |
| 20 | 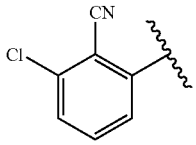 | 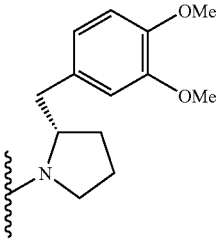 | 4.73 [A] | 432 |
| 21 | 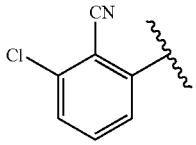 | 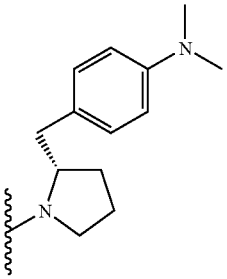 | 3.27 [A] | 414 |
| 22 | 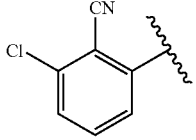 | 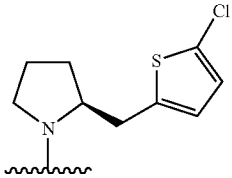 | 5.82 [A] | 411 |
| 23 | 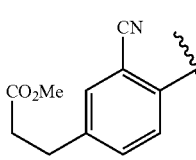 | 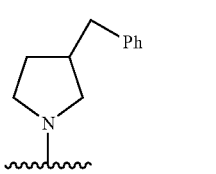 | 2.63 [B] | 423 |

What is claimed is:

1. A compound having the structure

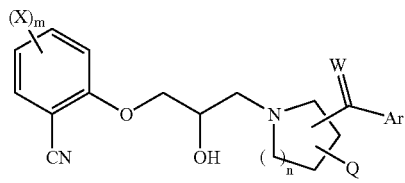

wherein
m is 0, 1, 2, 3 or 4;
each X is independently selected from hydrogen, halo, cyano, nitro, OCF$_3$, hydroxy, amino, carboxyl, alkyl, alkenyl, alkynyl, cycloalkyl, cycloheteroalkyl, haloalkyl, alkoxy, alkoxycarbonylalkyl, hydroxycarbonylalkyl, aryl, arylalkyl, heteroaryl, heteroarylalkyl, cycloalkylalkyl, R$^1$O, R$^1$R$^2$N, R$^1$OCO, R$^1$CO, R$^1$R$^2$NCO, R$^1$R$^2$NCONR$^{2a}$, R$^1$OCONR$^{2a}$, R$^1$CONR$^{2a}$, R$^1$S, R$^1$SO, R$^1$SO$_2$, R$^1$R$^2$NSO$_2$, R$^1$R$^2$NSO$_2$NR$^{2a}$, and R$^1$SO$_2$NR$^{2a}$;
R$^1$ is alkyl, alkenyl, alkynyl, cycloalkyl, cycloheteroalkyl, aryl, heteroaryl,, arylalkyl, or heteroarylalkyl;
R$^2$ and R$^{2a}$ are the same or different and are independently selected from hydrogen, alkyl, alkenyl, alkyl, cycloalkyl, cycloheteroalkyl, aryl, heteroaryl, arylalkyl, or heteroarylalkyl;
n is 1;
W is O or H, R$^3$;
R$^3$ is hydrogen or hydroxyl;
Ar is a substituted or unsubstituted aryl group or a substituted or unsubstituted heteroaryl group;
Q is hydrogen, F, or hydroxyl; all stereoisomers thereof; or
a pharmaceutically acceptable salt thereof.

2. The compound as defined in claim 1 wherein W is H, R$^3$ where R$^3$ is H or OH.

3. The compound as defined in claim 1 wherein Ar is C$_6$H$_5$,

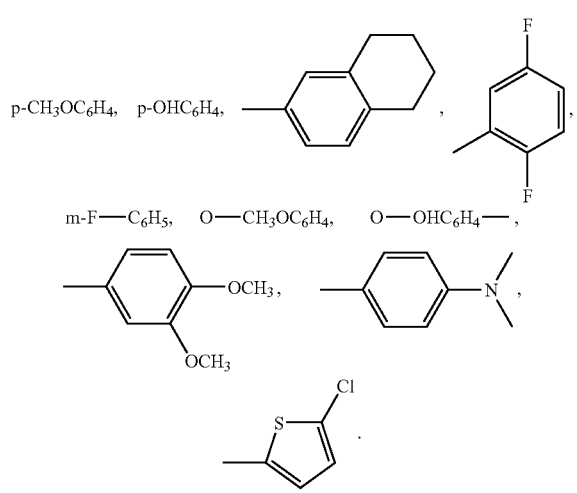

4. The compound as defined in claim 1 wherein Q is H.

5. The compound as defined in claim 1 wherein X is Cl or CH$_3$CO$_2$CH$_2$CH$_2$—.

6. The compound as defined in claim 1 wherein X is independently selected from hydrogen, halo, alkyl, alkenyl, alkynyl, cycloalkyl, cycloheteroalkyl, haloalkyl, alkoxy, alkoxycarbonylalkyl, hydroxycarbonylalkyl, aryl, heteroaryl, R$^1$R$^2$NCO, R$^1$CONR$^2$, R$^1$R$^2$NSO$_2$, and R$^1$SO$_2$NR$^{2a}$;
R$^1$ is alkyl, cycloalkyl, cycloheteroalkyl, aryl, heteroaryl, arylalkyl, or heteroarylalkyl;
R$^2$ and R$^{2a}$ are the same or different and are independently selected from hydrogen, alkyl, cycloalkyl, cycloheteroalkyl, aryl, heteroaryl, arylalkyl, or heteroarylalkyl;
m is 0, 1, or 2;
n is 1;
W is H,R$^3$;
R$^3$ is hydrogen or hydroxyl; Ar is a substituted or unsubstituted phenyl group; and
Q is hydrogen or hydroxyl.

7. The compound as defined in claim 1 having the structure

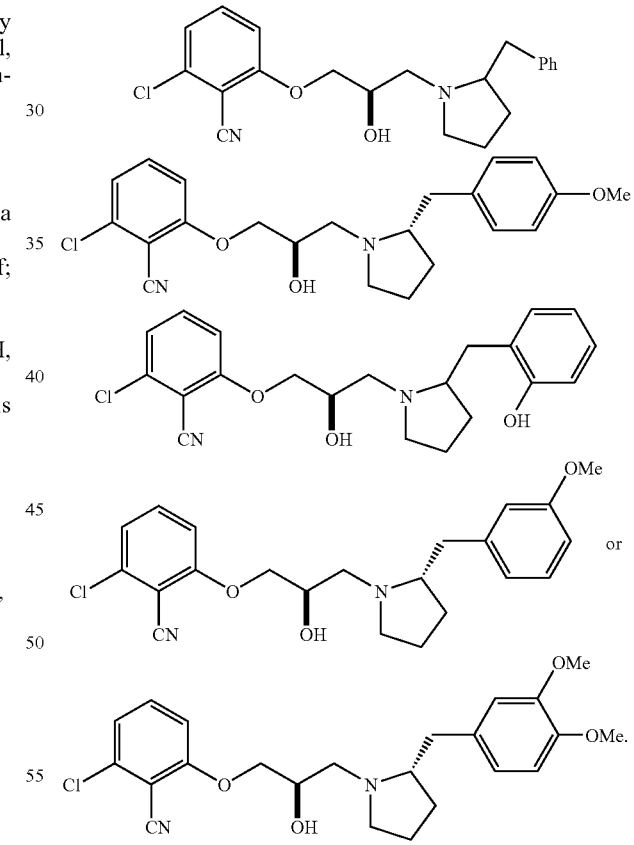

8. A pharmaceutical composition comprising an effective amount of a compound as defined in claim 1 and a pharmaceutically acceptable carrier thereof.

* * * * *

UNITED STATES PATENT AND TRADEMARK OFFICE
CERTIFICATE OF CORRECTION

| | | |
|---|---|---|
| PATENT NO. | : 7,265,145 B2 | Page 1 of 1 |
| APPLICATION NO. | : 10/854689 | |
| DATED | : September 4, 2007 | |
| INVENTOR(S) | : John K. Dickson et al. | |

It is certified that error appears in the above-identified patent and that said Letters Patent is hereby corrected as shown below:

Claim 1:
    Column 33, line 26, change "heteroaryl,," to -- heteroaryl, --.

Claim 5:
    Column 34, line 2, change "C1" to -- Cl --.

Signed and Sealed this

Eighth Day of March, 2011

David J. Kappos
*Director of the United States Patent and Trademark Office*